(12) United States Patent
Calderon-Urrea et al.

(10) Patent No.: US 9,125,413 B1
(45) Date of Patent: Sep. 8, 2015

(54) NEMATICIDE COMPOSITION COMPRISING CED-4 PEPTIDE

(71) Applicant: California State University Fresno, Fresno, CA (US)

(72) Inventors: Alejandro Calderon-Urrea, Fresno, CA (US); Harinder Singh, Fresno, CA (US); Viswanathan Venkata Krishnan, Fresno, CA (US)

(73) Assignee: California State University, Fresno, Fresno, CA (US)

( * ) Notice: Subject to any disclaimer, the term of this patent is extended or adjusted under 35 U.S.C. 154(b) by 0 days.

(21) Appl. No.: 14/322,200

(22) Filed: Jul. 2, 2014

(51) Int. Cl.
| | | |
|---|---|---|
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A01N 43/50* | (2006.01) | |
| *C07K 7/08* | (2006.01) | |
| *C07K 7/06* | (2006.01) | |
| *A01N 43/36* | (2006.01) | |

(52) U.S. Cl.
CPC ............... *A01N 43/50* (2013.01); *A01N 43/36* (2013.01); *C07K 7/06* (2013.01); *C07K 7/08* (2013.01)

(58) Field of Classification Search
None
See application file for complete search history.

(56) References Cited

U.S. PATENT DOCUMENTS 7,071,302 B1 * 7/2006 Horvitz et al. ................ 530/350

OTHER PUBLICATIONS

Abad, P., et al. (2008). Genome sequence of the metazoan plant-parasitic nematode Meloidogyne incognita. Nature Biotechnology (26), 909-915.
Li, X., et al. (2007). Resistance to root knot nematode in tomato roots expressing a nematicidal Bacillus thuringiensis crystal protein. Plant Biotechnology Journal 5, 455-464.
Bakhetia, M., et al. (2005). RNA Interference of Dual Oxidase in the Plant Nematode Meloidogyne incognita. Am. Phytopathological Soc. vol. 18, No. 10, 1099-1106.
Chan, Y., et al. (2010). Heterologous expression of taro cystatin protects transgenic tomato against Meloidogyne incognita infection by means of interfering sex determination arid suppressing gall formation. Plant Cell Rep (29),231-238.
Gheysen, G. and Vanholme, B. (2007). RNAi from plants to nematodes. Trends in Biotechnology. vol. 25, No. 3, 89-92.
Urwin, P., et al. (1995). Engineered oryzacystatin-I expressed in transgenic hairy roots confers resistance to Globodera pallida. Plant Journal 8(1), 121-131.
Burrows, P. and De Waele, D. (1997). Engineering Resistance Against Plant Parasitic Nematodes Using Anti-Nematode Genes. Cellular and Molecular Aspects of Plant-Nematode Interactions. vol. 10. Ed: Fenoll et al. Norwall, MA: Kluwer Academic Publishers, 217-236.

* cited by examiner

*Primary Examiner* — Marcela M Cordero Garcia
(74) *Attorney, Agent, or Firm* — Grace Liu, Esq.

(57) ABSTRACT

The present invention relates to nematicides, which are compositions that kill nematodes when placed in physical contact with nematodes. Nematodes do not decompose organic matter, but, instead, are parasitic and free-living organisms that feed on living material. *M. incognita* is a root knot nematode that has the ability to cause infection in more than 2,000 species of plants. Specifically, the present invention relates to CED-4 peptides that effectively kill nematodes. These CED-4 peptides are segments of the CED-4 protein. This invention is directed to a nematicide composition comprising an effective amount of a CED-4 peptide consisting of no more than 50 amino acids. In one aspect of the invention, the nematicide composition consists of no more than 30 amino acids. In another aspect of the invention, the nematicide consists of no more than 20 amino acids.

9 Claims, 7 Drawing Sheets

SEQUENCE LISTING

```
<160> NUMBER OF SEQ ID NOS: 1

<210> SEQ ID NO 1
<211> LENGTH: 549
<212> TYPE: PRT
<213> ORGANISM: Caenorhabditis elegans
<300> PUBLICATION INFORMATION:
<308> DATABASE ACCESSION NUMBER: GenBank/CAA48781.1
<309> DATABASE ENTRY DATE: 2014-05-30
<313> RELEVANT RESIDUES IN SEQ ID NO: (1)..(549)
```

<400> SEQUENCE: 1

```
Met Leu Cys Glu Ile Glu Cys Arg Ala Leu Ser Thr Ala His Thr Arg
1               5                   10                  15

Leu Ile His Asp Phe Glu Pro Arg Asp Ala Leu Thr Tyr Leu Glu Gly
            20                  25                  30

Lys Asn Ile Phe Thr Glu Asp His Ser Glu Leu Ile Ser Lys Met Ser
            35                  40                  45

Thr Arg Leu Glu Arg Ile Ala Asn Phe Leu Arg Ile Tyr Arg Arg Gln
50                  55                  60

Ala Ser Glu Leu Gly Pro Leu Ile Asp Phe Phe Asn Tyr Asn Asn Gln
65                  70                  75                  80

Ser His Leu Ala Asp Phe Leu Glu Asp Tyr Ile Asp Phe Ala Ile Asn
            85                  90                  95

Glu Pro Asp Leu Leu Arg Pro Val Val Ile Ala Pro Gln Phe Ser Arg
            100                 105                 110

Gln Met Leu Asp Arg Lys Leu Leu Leu Gly Asn Val Pro Lys Gln Met
            115                 120                 125

Thr Cys Tyr Ile Arg Glu Tyr His Val Asp Arg Val Ile Lys Lys Leu
130                 135                 140

Asp Glu Met Cys Asp Leu Asp Ser Phe Phe Leu Phe Leu His Gly Arg
145                 150                 155                 160

Ala Gly Ser Gly Lys Ser Val Ile Ala Ser Gln Ala Leu Ser Lys Ser
            165                 170                 175

Asp Gln Leu Ile Gly Ile Asn Tyr Asp Ser Ile Val Trp Leu Lys Asp
            180                 185                 190

Ser Gly Thr Ala Pro Lys Ser Thr Phe Asp Leu Phe Thr Asp Ile Leu
            195                 200                 205

Leu Met Leu Lys Ser Glu Asp Asp Leu Leu Asn Phe Pro Ser Val Glu
210                 215                 220

His Val Thr Ser Val Val Leu Lys Arg Met Ile Cys Asn Ala Leu Ile
225                 230                 235                 240

Asp Arg Pro Asn Thr Leu Phe Val Phe Asp Asp Val Val Gln Glu Glu
            245                 250                 255

Thr Ile Arg Trp Ala Gln Glu Leu Arg Leu Arg Cys Leu Val Thr Thr
            260                 265                 270

Arg Asp Val Glu Ile Ser Asn Ala Ala Ser Gln Thr Cys Glu Phe Ile
275                 280                 285

Glu Val Thr Ser Leu Glu Ile Asp Glu Cys Tyr Asp Phe Leu Glu Ala
            290                 295                 300

Tyr Gly Met Pro Met Pro Val Gly Glu Lys Glu Glu Asp Val Leu Asn
305                 310                 315                 320

Lys Thr Ile Glu Leu Ser Ser Gly Asn Pro Ala Thr Leu Met Met Phe
            325                 330                 335

Phe Lys Ser Cys Glu Pro Lys Thr Phe Glu Lys Met Ala Gln Leu Asn
            340                 345                 350

Asn Lys Leu Glu Ser Arg Gly Leu Val Gly Val Glu Cys Ile Thr Pro
            355                 360                 365

Tyr Ser Tyr Lys Ser Leu Ala Met Ala Leu Gln Arg Cys Val Glu Val
            370                 375                 380

Leu Ser Asp Glu Asp Arg Ser Ala Leu Ala Phe Ala Val Val Met Pro
385                 390                 395                 400

Pro Gly Val Asp Ile Pro Val Lys Leu Trp Ser Cys Val Ile Pro Val
```

-continued

```
                405                 410                 415
Asp Ile Cys Ser Asn Glu Glu Glu Gln Leu Asp Asp Glu Val Ala Asp
            420                 425                 430

Arg Leu Lys Arg Leu Ser Lys Arg Gly Ala Leu Leu Ser Gly Lys Arg
        435                 440                 445

Met Pro Val Leu Thr Phe Lys Ile Asp His Ile Ile His Met Phe Leu
    450                 455                 460

Lys His Val Val Asp Ala Gln Thr Ile Ala Asn Gly Ile Ser Ile Leu
465                 470                 475                 480

Glu Gln Arg Leu Leu Glu Ile Gly Asn Asn Asn Val Ser Val Pro Glu
                485                 490                 495

Arg His Ile Pro Ser His Phe Gln Lys Phe Arg Arg Ser Ser Ala Ser
            500                 505                 510

Glu Met Tyr Pro Lys Thr Thr Glu Glu Thr Val Ile Arg Pro Glu Asp
        515                 520                 525

Phe Pro Lys Phe Met Gln Leu His Gln Lys Phe Tyr Asp Ser Leu Lys
    530                 535                 540

Asn Phe Ala Cys Cys
545
```

NEMATICIDE COMPOSITION COMPRISING CED-4 PEPTIDE

BACKGROUND OF THE INVENTION

1. Field of the Invention

The field of the invention is compositions for and methods of killing nematodes.

2. Description of the Prior Art

Agricultural losses due to parasites have always been a major area of concern for most of the nations throughout the world. It is reported that agriculture industry suffers an estimated loss of $157 billion each year due to plant-parasitic nematodes (Abad et al., 2008). Due to such massive monetary losses, plant-parasitic nematodes are attracting the attention of scientists with *Meloidogyne incognita* being the major parasite of concern. *M. incognita* is a root knot nematode that has the ability to cause infection in more than 2,000 species of plants.

Although chemical nematicides have been successfully used to control plant-parasitic nematodes, these chemicals are toxic (Li et al., 2007). Many conventional nematicides used to control plant-parasitic nematodes have been shown to contribute to groundwater contamination and depletion of the ozone layer, to be hazardous to the health of humans and animals, and to be possibly harmful to other beneficial microorganisms present in the rhizosphere. A well-known nematicide, methyl-bromide, has been the most effective compound for the control of plant-parasitic nematodes in the past but has been banned from use because of its damaging effects on ozone layer, human health and environment (Li et al., 2007).

Novel methods of nematode control include building nematode resistance in plants by introducing genes that, when expressed, affect the development of the nematode. One such system induces the expression of proteinase inhibitors; in particular, the cysteine proteinase oryzacystatin-I gene from rice has been used to confer resistance against the potato cyst nematode *Globodera pallida* (Urwin et al. 1995). Similar expression of a taro cystatin gene in transgenic tomato restricted egg mass formation by more than 30% when compared to untransformed plants (Chan et al. 2010).

Transgenic tomato plants expressing the Bt-endotoxin Crylab inoculated with *Meloidogyne* spp. demonstrated a significant reduction of nematode egg masses per gram of root tissues (Burrows and De Waele 1997). A very promising strategy is the use of RNA interference (RNAi) technology to silence genes that could support nematode development (Bakhetia et al. 2005; Gheysen and Vanholme 2007). Transgenic methods of killing nematodes are very time consuming and expensive. It takes a lot of time and effort to introduce genes into plants and then ensure those genes are expressed properly. Killing nematodes is much faster and more efficient if a person can place a nematicide composition directly in contact with the nematodes without involving plant gene expression.

SUMMARY OF THE INVENTION

This invention is directed to a nematicide composition comprising an effective amount of a CED-4 peptide consisting of no more than 50 amino acids. In one aspect of the invention, the nematicide composition consists of no more than 30 amino acids. In another aspect of the invention, the nematicide consists of no more than 20 amino acids. In yet another aspect of the invention, the nematicide may be administered to plant parasitic nematodes. In one aspect of the invention, the nematicide may be administered to nematodes from genus *Meloidogyne*. In one more aspect of the invention, the effective nematicide amount consists of a CED-4 peptide concentration of about 0.8 mg/ml.

The nematicide may contain a CED-4 peptide consisting of amino acid sequence 112-130 of SEQ ID No. 1. In another aspect of the invention, the CED-4 peptide may consist of amino acid sequence 99-113 of SEQ ID No. 1. In yet another aspect of the invention, the CED-4 peptide consists of amino acid sequence 529-540 of SEQ ID No. 1.

BRIEF DESCRIPTION OF THE DRAWINGS

FIG. 1 shows the life cycle of *C. elegans.*

FIG. 2 shows the pathway of *C. elegans* programmed cell death.

FIG. 3 shows the CED-4 apoptosome.

FIG. 4A shows a polyacrylamide gel image revealing recombinant CED-4 protein production in *E. coli* bacteria cells.

FIG. 4B shows a Western blot revealing absence of CED-4 protein production in *C. elegans* ced-4 mutant.

FIG. 5 shows the number of hatched offspring of each of wild-type, ced-3, ced-4 mutant *C. elegans* that were fed control bacteria and bacteria producing CED-4.

FIG. 6 shows the effects of purified CED-4 protein on *M. incognita* J2 nematode vitality after 6 days of in vitro incubation with extracted CED-4 protein.

FIG. 7 shows the CED-4 protein divided into 12 peptides.

FIG. 8 shows important amino acid regions of the CED-4 protein after box averages were calculated from the normalized cumulative total scores of each amino acid residue of CED-4, with a box score cut-off value of 0.5.

FIG. 9 shows the important amino acid regions of the CED-4 protein, those that are above the cut-off box score value of 0.5.

DETAILED DESCRIPTION OF THE INVENTION AND PREFERRED EMBODIMENTS

The present invention relates to nematicides, which are compositions that kill nematodes when placed in physical contact with nematodes. Specifically, the present invention relates to CED-4 peptides that effectively kill nematodes. These CED-4 peptides are segments of the CED-4 protein.

Nematodes are round-nematodes from the phylum Nematoda. They are a diverse animal phylum inhabiting a very broad range of environments. Nematodes have tubular digestive systems with openings at both ends. The vast majority of nematodes reside in the top 15 cm of soil. Nematodes do not decompose organic matter, but, instead, are parasitic and free-living organisms that feed on living material.

A. DEFINITIONS

The term "effective amount" as used herein defines an amount of a given CED-4 peptide placed in physical contact with a nematode which results in the objectively determinable death of the nematode.

The term "administer" as used herein means "applied to," and may be used interchangeably with the following: contacted with, passed over, flowed over, and sprayed on.

The term "incubate" as used herein defines an act keeping a living organism in conditions suitable for continued development and/or growth.

The term "residue" as used herein defines a specific monomer within the polymeric chain of a polysaccharide, protein, peptide or nucleic acid.

B. *C. ELEGANS* CHARACTERISTICS AND LIFE CYCLE

Figure 1:
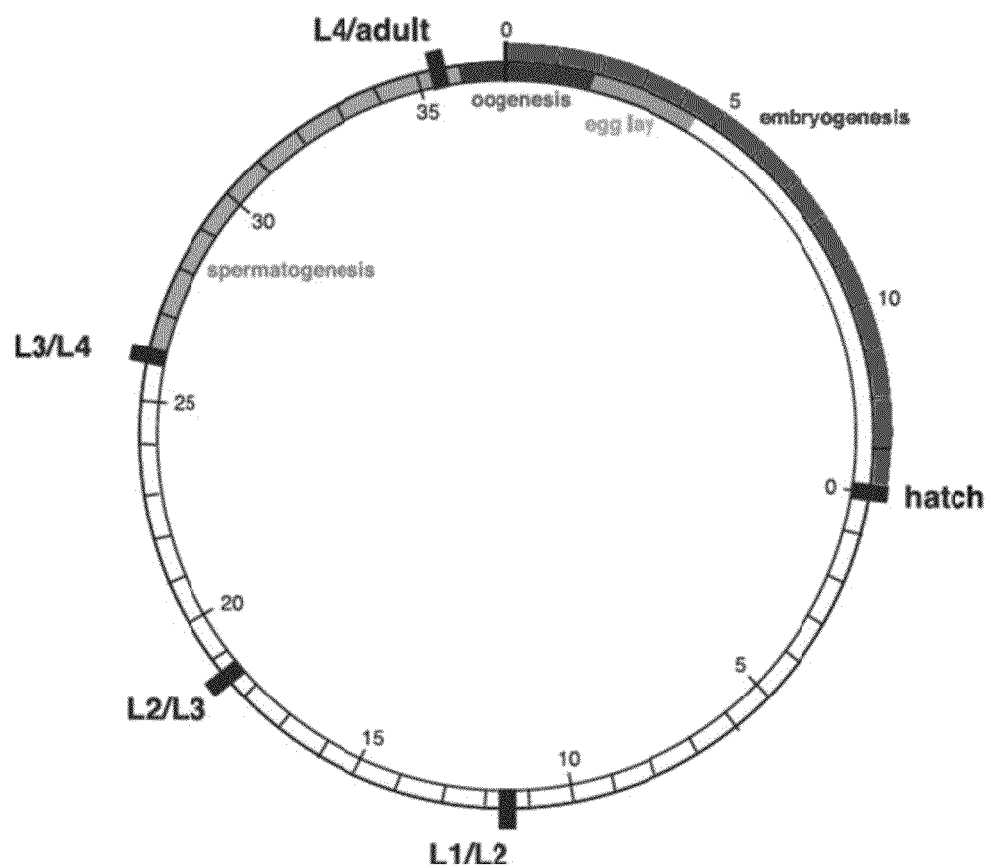

The nematode, *Caenorhabditis elegans*, is a model organism used in many laboratories because of its easy growth, maintenance, observation and less complex life cycle. As shown in FIG. 1, throughout its life cycle *C. elegans* passes from four larval stages (L1-L4) to develop into a sexual adult. The transition from fertilized egg to sexual adult takes 3 days (Blaxter, 2011). In FIG. 1, the numbers outside the circle represent hours since fertilization and the numbers inside the circle represents hours since hatching. L1-L4 are the larval stages. L1/L2 represents transition from L1 to L2. Likewise, L2/L3 represents transition from L2 to L3. Also, L3/L4 represents transition from L3 to L4. And L4/adult represents the transition from L4 to adult.

C. *C. ELEGANS* PROGRAMMED CELL DEATH

Figure 2:
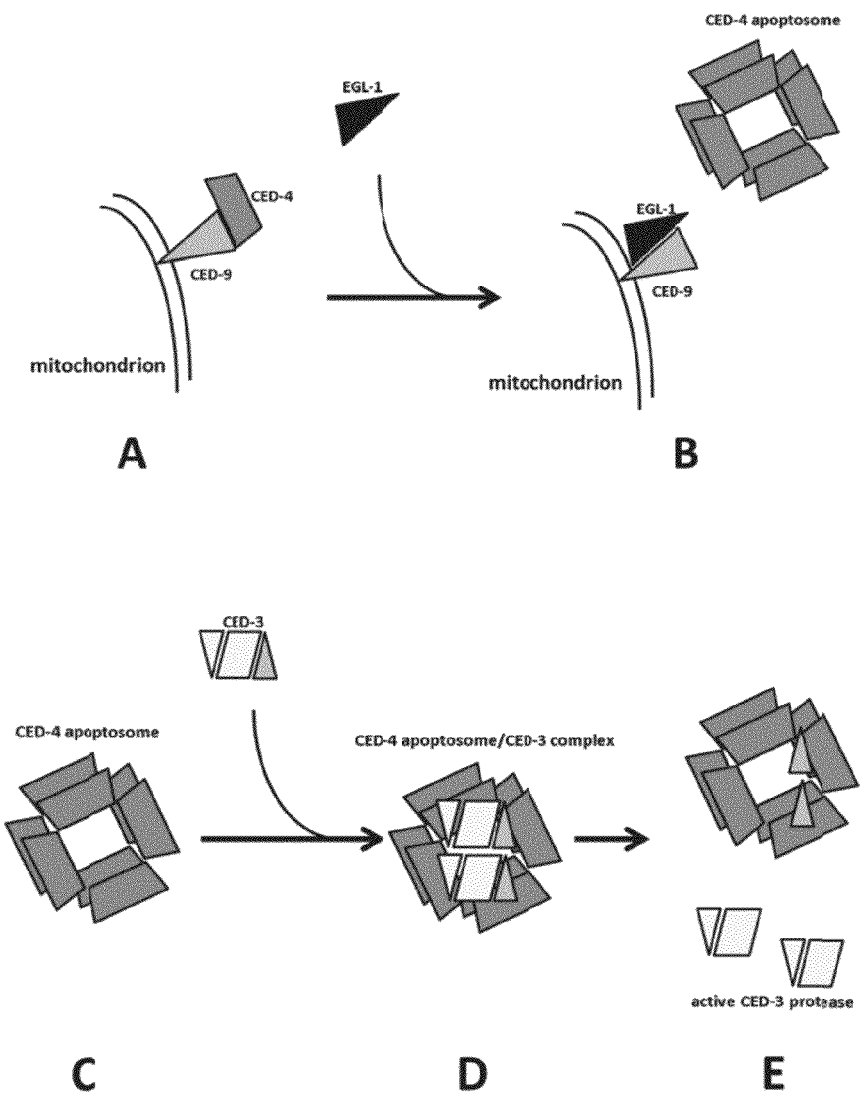

Programmed Cell Death ("PCD") is a physiological cell death mechanism that involves elimination of waste and diseased/unwanted cells from plants or from body of animals (Pennell and Lamb, 1997). FIG. 2 shows the biochemical model for the process of *C. elegans* PCD in which apoptosis takes place. There are three phases of PCD in *C. elegans*. The first phase—unshown in FIG. 2—is the specification phase, in which a cell gets the signals to start the PCD mechanism. FIG. 2 shows the second phase, the killing phase in which apoptosis is activated in the target cell. The third phase—unshown in FIG. 2—is the execution phase, in which the cell is disrupted and the inner material of dead cell is eaten away by surrounding cells.

As shown in FIG. 2, there are various proteins essential for the PCD process in *C. elegans*. Among these CED-9, EGL-1, CED-3 and CED-4 are the most important to regulate programmed cell death. CED-9, EGL-1, CED-3 and CED-4 act in a cascade that is initiated by the activation of EGL-1 protein by many transcriptional regulators such as CES-1, CES-2, HLH-1/HLH-2, and TRA-1.

As shown in FIG. 2, step A, CED-4/CED-9 complex is present on the surface of mitochondria. As shown in FIG. 2, step B, once activated, EGL-1 assists in the release of CED-4 from the CED-4/CED-9 complex present at the surface of mitochondria. Free CED-4 self-oligomerises and forms an apoptosome, as shown in FIG. 2, step C, which gets translocated from the mitochondrial surface to the perinuclear membrane where CED-4 apoptosome interacts with CED-3 to create the CED-4 apoptosome/CED-3 complex, as shown in FIG. 2, step D. The created CED-4 apoptosome/CED-3 complex triggers autocatalytic activation of the CED-3 protease, as shown in FIG. 2, step E (Conradt and Xue, 2005). The active CED-3 protease initiates the execution phase—unshown in FIG. 2—in which the cell is disrupted and the inner cell material is eaten by surrounding cells.

D. CED-4 PROTEIN AND STRUCTURE OF CED-4 APOPTOSOME

CED-4 is a 549 amino acid residues long protein, which is a result of 2.2 kb RNA transcript encoded by a 4.4 kb ced-4 gene. The CED-4 protein is about 62 KD in weight. In *C. elegans*, plenty of CED-4 mRNA is expressed during the time of embryogenesis, as most of the programmed cell deaths take place during that phase (Yuan and Horvitz, 1992). During the PCD mechanism, asymmetric CED-4 homodimers forms a tetramer called apoptosome. Formation of CED-4 apoptosome is an intermediate step and is considered important for PCD to happen.

Figure 3:
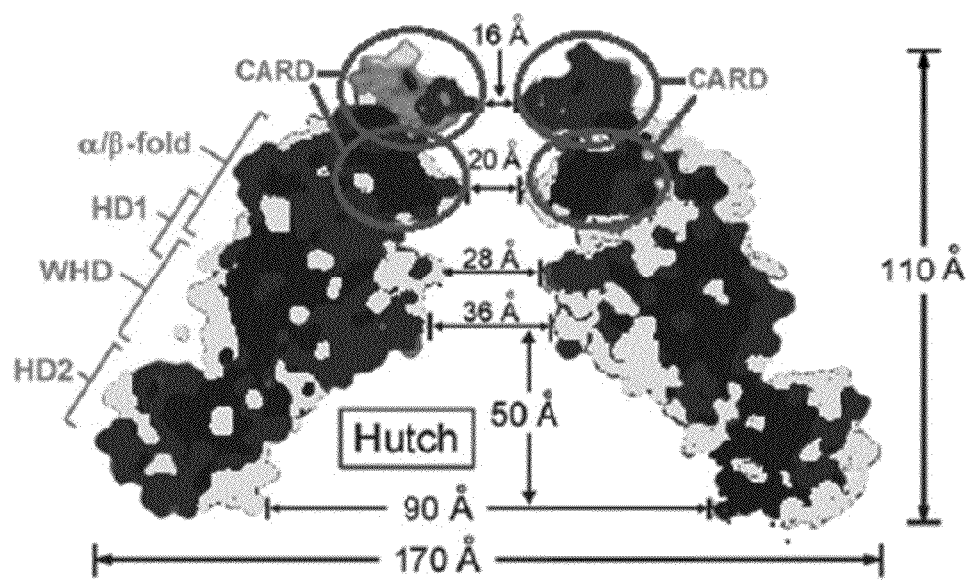

As shown in FIG. 3, the crystal structure of CED-4 apoptosome reveals that eight molecules of CED-4 are present as two tetramers of asymmetric dimers. CED-4 contains a caspase recruitment domain (CARD), a nucleotide-binding $\alpha/\beta$ fold, a small helical domain (helical domain 1, or HD1), a winged-helix domain (WHD), and helical domain 2 (HD2) (Qi et al., 2010).

Control of activation of CED-3 protease, specifically a caspase zymogen, by CED-4 apoptosome makes CED-4 an interesting protein to study as a nematicide. CED-4 acts upstream to CED-3 in the PCD pathway, and both play important roles in causing apoptosis in *C. elegans*.

E. RECOMBINANT CED-4 PROTEIN PRODUCTION INDUCED IN *E. COLI*

Figure 4A:
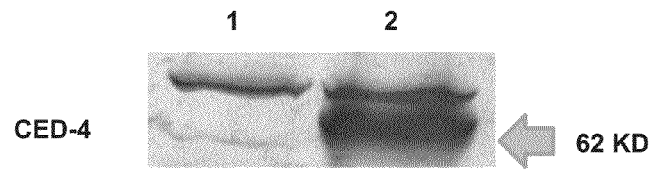

Constructed expression cassettes generate CED-4 protein in bacteria. In FIG. 4A, lane 2, the gel image shows presence of recombinant CED-4 protein in *E. coli* cells, as opposed to FIG. 4A, lane 1 which shows lack of presence of CED-4 protein in uninduced *E. coli* cells. In this experiment, the ced-4 gene was sub-cloned into the pBAD-DEST49 vector. The pBAD-DEST49-ced-4 construct, and the pBAD-DEST49 empty vector were tested for synthesis of the protein CED-4. The *E. coli* bacteria strain (TOP 10 chem.) was grown, and once the optical density $OD_{600}$ reached 0.5, the bacteria was induced by adding L-Arabinose 20% and incubated for four hours at 37° C., 226 rpm in rotary shaker (C24, incubator shaker, Edison, N.J. USA). The production of CED-4 protein was analyzed by SDS 10% acrylamide gel and commassie blue staining.

As shown in FIG. 4A, lane 2, the gel image shows that the recombinant protein CED-4, weighing approximately 62 kD, is present in the bacteria expressing the gene ced-4. The 62 kD recombinant CED-4 protein is indicated with an arrow. As shown in FIG. 4A lane 1, this recombinant protein CED-4 was absent in the bacteria transformed by empty vector pBAD-DEST49 used as a negative control.

F. CED-4 ABSENT IN LOSS-OF-FUNCTION CED-4 MUTANT *C. ELEGANS*

Figure 4B:
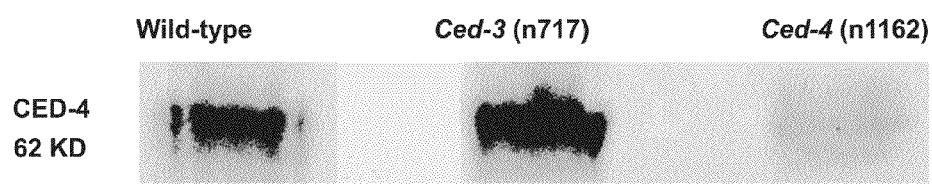

FIG. 4B shows a Western blot assay conducted on *C. elegans* embryo lysates. As shown in FIG. 4B, the CED-4 protein is present in wild-type (N2 strain) and ced-3 (strain n717) mutant nematodes, but undetectable in ced-4 (strain n1162) mutant nematodes. The ced-3 (n717) and the ced-4 (n1162) mutant strains are both strong loss of function mutant strains. The CED-4 sensitive antibody detects a 62 kD protein on Western blots of N2 wild-type *C. elegans* and mutant ced-3 (n717) embryo lysates. This 62-KD protein was not produced in ced-4 (n1162) embryo lysates.

G. NEMATODES FED *E. COLI* PRODUCING CED-4 HAVE DECREASED FECUNDITY

The genes ced-4 and ced-3 are required for PCD in somatic cells of *C. elegans*, and a loss-of-function (lf) mutation in any one of them results in increased survival rates of cells that would otherwise be eliminated by PCD. In the experiment summarized by FIG. 5, bacteria carrying the ced-4 gene construct and bacteria carrying an empty vector were grown as described above in Section E, and used to feed *C. elegans* wild-type nematodes, mutant *C. elegans* ced-3 nematodes, and mutant *C. elegans* ced-4 nematodes at L1/L2 stages (refer to FIG. 1). For the experiment described in FIG. 5, *C. elegans* wild-type (wt), ced-3 (n717) and ced-4 (n1162) strains were synchronized, and the hatched nematodes were raised on a diet consisting of *E. coli* bacteria producing CED-4. Both nematodes and bacteria were sustained on NGM media and incubated at a temperature between 25° C. and 28° C.

Figure 5:
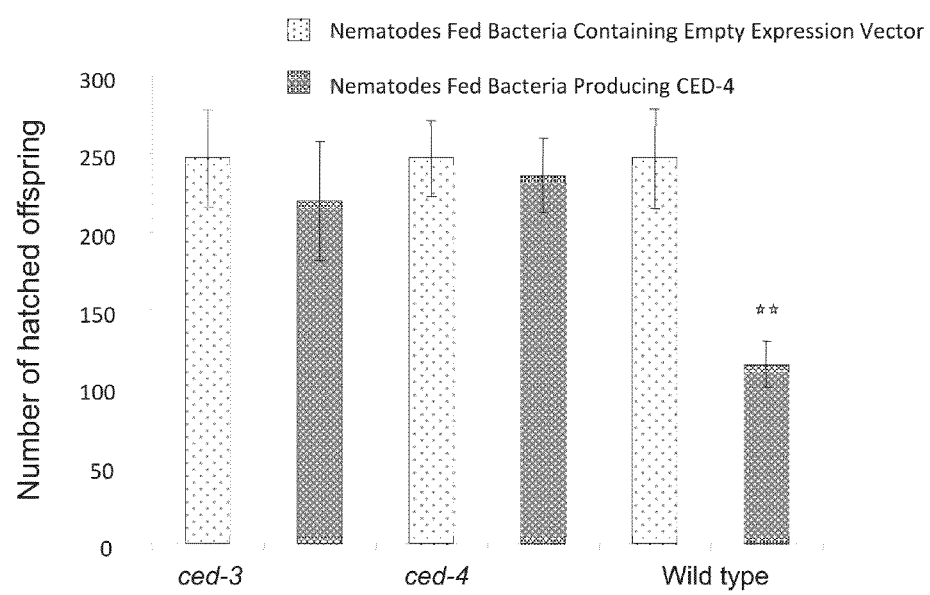

The effects of CED-4 ingestion on all three different strains of *C. elegans* used were quantified by population size throughout several generations. After the hatched nematodes fed on either the control bacteria or the CED-4 producing bacteria for 72 hours, the nematodes in each experiment were scored for fecundity over the course of 120 hrs. Fecundity was measured by counting the number of hatched offspring. There were ten experiments replicated for each of the three analyzed *C. elegans* strains. FIG. 5 shows the mean number of hatched offspring and standard of error for each of the ten experiments for the *C. elegans* wild type, the ced-3 mutant, and the ced-4 mutant strains.

As shown in FIG. 5, *C. elegans* wild type nematodes that were fed bacteria producing CED-4 decreased in population size over the course of 120 hours. In other words, exposure to CED-4 lowers the fecundity, or offspring production ability, of *C. elegans* wild type nematodes. As shown in FIG. 5, in ten independent feeding experiments with 2 wild-type nematode embryos in each experiment, CED-4 fed individuals produced significantly fewer offspring (less than 50%) than those fed bacteria containing empty expression vectors, serving as negative controls (FIG. 5; t-test, $p \leq 0.01$).

Approximately 2 wild-type nematode embryos exposed to non-CED-4 expressing bacteria collectively produced nematodes numbering from about 215 to about 279 hatched offspring, with a mean of 247 hatched offspring. The 2 wild-type nematode embryos exposed to bacteria expressing CED-4 collectively produced nematodes numbering from about 100 to about 130 hatched offspring, with a mean of about 115 hatched offspring. The reduction in fecundity in wild type *C. elegans* nematodes is due to the effects of exogenously produced CED-4, which was ingested by the nematodes as they ingest bacteria producing CED-4.

Also shown in FIG. 5, exogenous CED-4 does not reduce the fecundity of ced-3 mutant nematodes. CED-3 function is dependent on the presence of the upstream CED-4, and ced-3 mutant nematodes did not suffer loss of fecundity when fed bacteria expressing CED-4. The lack of functional CED-3 protein in the ced-3 mutant nematodes rendered the presence of exogenous CED-4 protein functionally irrelevant, and therefore irrelevant in decreasing nematode fecundity. In each of the ten independent experiments, 2 ced-3 mutant *C. elegans* embryos exposed to non-CED-4 producing bacteria collectively produced between about 216 hatched offspring and about 278 hatched offspring, with a mean of about 247 hatched offspring. The ced-3 mutant nematodes ingesting CED-4 producing bacteria collectively produced between about 182 hatched offspring and about 258 hatched offspring, with a mean of about 220 hatched offspring. The slight decrease in ced-3 mutant fecundity due to exposure to exogenous CED-4, shown in FIG. 5, is statistically insignificant.

As shown in FIG. 5, ced-4 mutant nematodes do not lose fecundity when exposed to exogenous CED-4 from ingesting bacteria producing CED-4. The ced-4 (n1162) loss of function mutant *C. elegans* nematodes do not produce functional CED-4 protein. In each of the ten independent experiments, 2 ced-4 mutant embryos exposed to non-CED-4 producing bacteria collectively produced between about 223 hatched offspring and about 271 hatched offspring, with a mean of about 247 hatched offspring. The 2 ced-4 mutant embryos exposed to CED-4 producing bacteria collectively produced between about 212 hatched offspring and about 260 hatched offspring, with a mean of about 236 hatched offspring.

The slight decrease in ced-4 mutant fecundity due to exposure to exogenous CED-4 shown in FIG. 5 is statistically insignificant. This lack of loss of fecundity in ced-4 mutants is because the exogenous CED-4 exposure is not enough to cause any loss of fecundity in *C. elegans* that have lost all ability to produce functional CED-4 protein. In all likelihood, the ingested CED-4 boosted the ced-4 mutant individual levels of CED-4 to no more than the normal endogenous CED-4 level of wild type *C. elegans* nematodes. Furthermore, it is possible that the ced-4 (n1162) mutant used in these experiments may have other defects that impede the use of exogenous CED-4.

The results shown in FIG. 5 suggest that the 50% reduction in fecundity seen in wild-type *C. elegans* nematodes is due to exposure to exogenously produced CED-4, which is being ingested by the nematodes as they ingest bacteria expressing CED-4. Exposure to exogenous CED-4 decreases the number of *C. elegans* offspring.

H. IN VITRO EXPOSURE OF *M. INCOGNITA* TO CED-4 PROTEIN DECREASES VIABILITY

The *Meloidogyne incognita* is a plant nematode in the family Heteroderidae. The *M. incognita* is a plant parasite classified as a root-knot nematode because it prefers to attack the root of its host plant. When *M. incognita* nematodes attack the roots of plants, they set up a feeding location, where they deform the normal root cells and establish giant cells. The roots become gnarled or nodulated, forming galls, hence the term "root-knot" nematode. The *M. incognita* J2 are second stage juvenile nematodes that just hatched.

Figure 6:
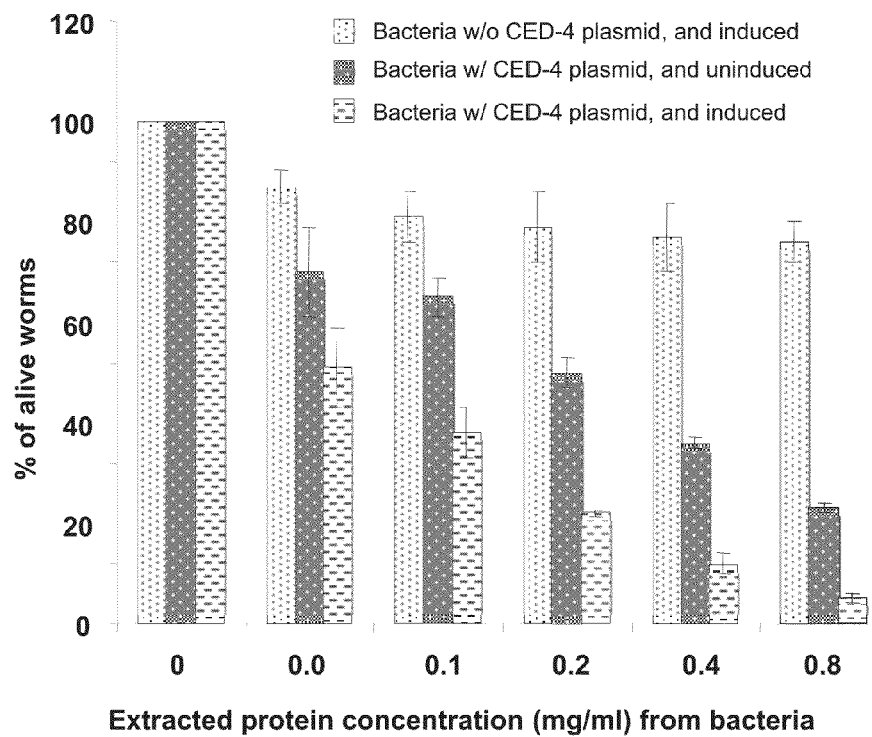

FIG. 6 shows that exposure of *M. incognita* J2 nematodes to CED-4 protein leads to decreased viability in the nematodes. In the experiment described in FIG. 6, the *M. incognita* J2 nematodes were exposed to one of three options: (1) a negative control consisting of *M. incognita* nematodes incubated with purified soluble protein extracts from competent bacterial cells without a CED-4 plasmid but induced, (2) a negative control consisting of *M. incognita* nematodes incubated with purified soluble protein extracts from bacteria cells containing a CED-4 plasmid, but uninduced, and (3) *M. incognita* nematodes incubated with purified soluble protein extracts from bacteria containing the CED-4 plasmid and induced. Susceptible tomato plants (Rutger's Select, Tomato, Augusta, Ga.) were used to maintain *M. incognita* in the following process.

The soluble protein was extracted from *E. coli* bacteria following the protocols described in the ProBond™ Purification System (Life Technologies/Thermo Fisher Scientific). The bacteria was grown overnight, the cells harvested by centrifugation and resuspended in Native Binding Buffer. After lysozyme treatment, the cells were disrupted by sonication and cellular debris removed by centrifugation. Proteins in this preparation were enriched for CED-4 by purification under native conditions using the ProBond™ resin. The fraction containing the HIS-tag (and therefore containing the CED-4 protein) was eluted with Native Elution Buffer (50 mM $NaH_2PO_4$, pH 8.0).

The first step comprised infecting sand-germinated tomato plants that were between five days and ten days old (each plant having shoots that measure about 10 cm long, and having roots that measure between about 4 cm and about 5 cm long) with *M. incognita* J2 nematodes. After infection, the *M. incognita* J2 nematodes created large galls on the tomato plant roots. Then, after between 5 weeks and 8 weeks of the *M. incognita* J2 nematode infection, the heavily galled plant roots were cut into small pieces and shaken vigorously for about 5 minutes with 10% bleach and subsequently poured through a 250 micron mesh screen. Eggs were collected from the flow-through on a 25 micron mesh screen and further purified by centrifugation in 35% sucrose at 500 g for 10 minutes. The supernatant was then subjected to two 10 minute treatments in 10% bleach followed by centrifugation at 500 g for 5 minutes and several rinses in sterile water.

In the next step, the *M. incognita* nematode eggs were incubated and hatched in a 28° C. incubator, and juveniles were allowed to crawl through a sterile mesh strainer to the water container. Once collected from the water container, *M. incognita* J2 nematodes were resuspended in soaking buffer (10.9 mM $Na_2HPO_4$, 5.5 mM $KH_2PO_4$, 2.1 mM NaCl, 4.7 mM $NH_4Cl$, 3 mM spermidine, and 0.05% gelatin in $diH_2O$) for in-vitro incubation with CED-4 enriched protein extracted from *E. coli* bacteria.

After resuspension in soaking buffer, approximately 500 nematodes were placed in each well of a sterile 96-well plate. Several wells served as a negative control, with each of these negative control wells containing about 100 μl of soaking buffer supplemented with varied concentrations of purified protein extracted from induced *E. coli* bacteria that do not contain the CED-4 plasmid. Also, several wells served as a negative control, with each of these wells containing about 100 μl of soaking buffer supplemented with varied concentrations of purified protein extracted from *E. coli* containing the CED-4 plasmid, but not induced. Lastly, several wells contained 100 μl of soaking buffer supplemented with varied concentrations of purified protein extracted from *E. coli* bacteria containing the CED-4 plasmid and induced. The experiment summarized in FIG. 6 was replicated 3 times at each indicated protein concentration.

1. In vitro exposure of *M. incognita* to purified protein extracted from induced *E. coli* that do not contain a CED-4 plasmid does not significantly decrease nematode viability.

As shown in FIG. 6, in the wells containing purified protein extracted from induced *E. coli* bacteria that do not contain the CED-4 plasmid, the percentage of nematodes that are still alive after six days decreased, but not significantly, as the protein concentration increased. At a protein concentration of 0 mg/ml, 100% of the *M. incognita* nematodes were alive after 6 days of incubation in a solution containing that protein concentration. At a protein concentration of about 0.05 mg/ml, a percentage of *M. incognita* nematodes from between about 85% and about 90%, with a mean of about 88%, were alive after 6 days of incubation in a solution containing that protein concentration. At a protein concentration of about 0.1 mg/ml, a percentage of *M. incognita* nematodes from between about 75% and about 86%, with a mean of about 80%, were alive after 6 days of incubation in a solution containing that protein concentration. At a protein concentration of about 0.2 mg/ml, a percentage of *M. incognita* nematodes from between about 72% and about 86%, with a mean of about 78%, were alive after 6 days of incubation in a solution containing that protein concentration. At a protein concentration of about 0.4 mg/ml, a percentage of *M. incognita* nematodes from between about 70% and about 83%, with a mean of about 79%, were alive after 6 days of incubation in a solution containing that protein concentration. At a protein concentration of about 0.8 mg/ml, a percentage of *M. incognita* nematodes from between about 76% and about 84%, with a mean of about 80%, were alive after 6 days of incubation in a solution containing that protein concentration.

There is no CED-4 protein produced by *E. coli* bacteria that do not contain the CED-4 plasmid. Therefore, CED-4 protein amounts do not increase in the increased extracted protein concentrations used to incubate nematodes. The slight insignificant decrease in nematode viability as the protein concentration increased is not due to increased exposure to CED-4 protein, but is most likely due to osmotic changes in the nematodes caused by the increasingly viscous protein solutions. As the protein concentration increases, the incubating solution becomes more viscous, causing osmotic changes within the exposed nematodes that cause a slight increase in the number of deaths of exposed nematodes.

2. In vitro exposure of *M. incognita* to purified protein extracted from uninduced *E. coli* that contain a CED-4 plasmid significantly decreases nematode viability.

As shown in FIG. 6, in the wells containing purified protein extracted from uninduced *E. coli* bacteria that do contain the CED-4 plasmid, the percentage of nematodes that are still alive after six days decreased significantly as the protein concentration increased. At a protein concentration of 0 mg/ml, 100% of the *M. incognita* nematodes were alive after 6 days of incubation in a solution containing that protein concentration. At a protein concentration of about 0.05 mg/ml, a percentage of *M. incognita* nematodes from between about 60% and about 80%, with a mean of about 70%, were alive after 6 days of incubation in a solution containing that protein concentration. At a protein concentration of about 0.1 mg/ml, a percentage of *M. incognita* nematodes from between about 66% and about 70%, with a mean of about 68%, were alive after 6 days of incubation in a solution containing that protein concentration. At a protein concentration of about 0.2 mg/ml, a percentage of *M. incognita* nematodes from between about 48% and about 52%, with a mean of about 50%, were alive after 6 days of incubation in a solution containing that protein concentration. At a protein concentration of about 0.4 mg/ml, a percentage of *M. incognita* nematodes from between about 37% and about 40%, with a mean of about 38%, were alive after 6 days of incubation in a solution containing that protein concentration. At a protein concentration of about 0.8 mg/ml, a percentage of *M. incognita* nematodes from between about 21% and about 23%, with a mean of about 22%, were alive after 6 days of incubation in a solution containing that protein concentration.

The uninduced bacteria still expressed the ced-4 gene and produced the CED-4 protein. Therefore, there is a measurable amount of CED-4 protein produced by, and extracted from, uninduced *E. coli* containing the CED-4 plasmid. As the protein concentration increased in the incubating solutions, the amount of CED-4 protein also increased in those solutions. The nematode viability decreased significantly as the protein concentration increased, because of the increased CED-4 amounts present in the incubating solutions. The nematodes incubated in purified protein extracted from uninduced *E. coli* containing the CED-4 plasmid decreased in viability as the protein concentration increased at a much faster rate than the nematodes exposed to increased protein concentrations that do not contain CED-4. Therefore, exposure to greater amounts of CED-4 protein causes increasing numbers of nematode deaths.

3. In vitro exposure of *M. incognita* to purified protein extracted from induced *E. coli* that contain a CED-4 plasmid significantly decreases nematode viability As shown in FIG. 6, in the wells containing purified protein extracted from induced *E. coli* bacteria that do contain the CED-4 plasmid, the percentage of nematodes that are still alive after six days decreased significantly as the protein concentration increased. At a protein concentration of 0 mg/ml, 100% of the *M. incognita* nematodes were alive after 6 days of incubation in a solution containing that protein concentration. At a protein concentration of about 0.05 mg/ml, a percentage of *M. incognita* nematodes from between about 42% and about 58%, with a mean of about 50%, were alive after 6 days of incubation in a solution containing that protein concentration. At a protein concentration of about 0.1 mg/ml, a percentage of *M. incognita* nematodes from between about 38% and about 42%, with a mean of about 40%, were alive after 6 days of incubation in a solution containing that protein concentration. At a protein concentration of about 0.2 mg/ml, a percentage of *M. incognita* nematodes from between about 20% and about 21%, with a mean of about 21%, were alive after 6 days of incubation in a solution containing that protein concentration. At a protein concentration of about 0.4 mg/ml, a percentage of *M. incognita* nematodes from between about 6% and about 10%, with a mean of about 8%, were alive after 6 days of incubation in a solution containing that protein concentration. At a protein concentration of about 0.8 mg/ml, a percentage of *M. incognita* nematodes from between about 3% and about 5%, with a mean of about 4%, were alive after 6 days of incubation in a solution containing that protein concentration.

The induced bacteria produces much more CED-4 protein than the uninduced bacteria. Therefore, the extracted protein from induced *E. coli* containing the CED-4 plasmid contains a larger amount of the CED-4 protein than uninduced *E. coli* containing the same plasmid. The larger amounts of CED-4 protein present in the purified protein extracted from the induced CED-4 containing *E. coli* cause higher numbers of nematode deaths.

FIG. 6 shows that the number of incubated J2 nematodes surviving after six days decreased inversely proportionally to the concentration of CED-4 protein extracted from the induced bacteria containing the CED-4 plasmid. These results show that CED-4 has deleterious effects on *M. incognita* J2 nematode viability. The CED-4 protein is probably being ingested by the nematodes since the nematodes J2 actively pump materials into their digestive system. The ingested CED-4 protein then causes PCD within the nematodes.

As shown in FIG. 5, when wild-type *C. elegans* nematodes were fed bacteria expressing CED-4 for 6 days, the rate of cell death (in *C. elegans*) increased approximately by 2 fold. As shown in FIG. 6, when *M. incognita* nematodes were incubated with purified protein, including CED-4 protein, for six days, it was found that the rate of cell death increased from approximately 2 fold to 15 fold with the increase in concentration of CED-4, starting from 0.05 mg/ml to 0.8 mg/ml of total protein concentration, respectively.

I. DESIGN OF VARIOUS CED-4 PEPTIDES

While the entire CED-4 protein, consisting of 549-amino acids, may act as a nematicide, it would be beneficial to discover a minimal CED-4 domain that can induce death in nematodes. A nematicide comprising a minimal CED-4 domain that is sufficient to induce death in nematodes would be advantageous over a nematicide comprising the full CED-4 protein because the peptides are many times shorter in length and smaller in size, therefore being faster and cheaper to produce on a commercial scale. To discover the minimal CED-4 domain sufficient to induce nematode death, CED-4 peptides were designed using the 3D protein structure and bioinformatics related tools. Then, the selected peptides were tested to see if each one sufficiently induced the death of nematodes.

Twelve CED-4 peptide segments were designed in silico, with each peptide spanning between 12 and 25 amino acid residues. Four parameters were considered while designing CED-4 peptide segments: (1) CED-4 amino acid residue conservation, (2) CED-4 amino acid residue interaction with other programmed cell death protein residues, (3) CED-4 protein structure, and (4) CED-4 peptide segment surface accessibility.

1. Parameter 1: CED-4 amino acid residue conservation

The first considered parameter was amino acid residue conservation in the CED-4 protein. The conservation score of each residue was obtained using HotSpot Wizard, a web server for automatic identification of the residues present on the active site of the protein and important for the functionality of the protein. The HotSpot Wizard software used for this study was version 1.7, designed in 2009 by Loschmidt Laboratories, Institute of Experimental Biology, Faculty of Science, Masaryk University, Kamenice 5/A4, 625 00 Brno, Czech Republic. The HotSpot Wizard estimates the mutability of each amino acid residue based on the conservation level. A high level of mutability for a given amino acid corresponds to a greater likelihood the amino acid residue can be changed without affecting the protein function. Residues with high mutability are called 'hot spots' within the overall protein sequence (Pavelka et al., 2009).

Hotspot Wizard provided the conservation score for each of the CED-4 amino acid residues. These scores varied from negative to positive values depending upon the conservation of that particular amino acid residue. A lower conservation score corresponds to higher conservation of the residue. The Hotspot Wizard software took input in Protein Database (PDB) format (PDB code for CED-4 is 31qq). The job was then submitted and results were sent to the email address provided by the user. The result file contained various links. To view the conservation scores for each residue 'phylogenetic analysis for chain B' link was selected and then 'Rate4Site' sub link was selected.

2. Parameter 2: CED-4 amino acid residue interaction with other programmed cell death protein residues The second considered parameter was CED-4 residue interaction with the residues of other cell death mechanism proteins. To determine the important residues responsible for the CED-4 protein interaction with the other cell death mechanism proteins, CED-4 was studied via computer analysis, in silico, in interactions with the following proteins: ATP, CED-3, CED-9, and CED-4 itself. The in silico analysis was carried out using PDBsum, a web-based database which provides important information on each macromolecular structure deposited at the Protein Data Bank (PDB) (Laskowski, 2001). The PDBsum database used for this study was a new version, designed in 2001 by Roman Laskowski and Victor Chistyakov at the European Bioinformatics Institute. CED-4 residues that interacted with the residues of other important proteins of programmed cell death process were considered more important than those CED-4 residues that did not participate in such interactions (or interacted with the residues of only few of PCD proteins; for an instance if a CED-4 residue appeared in CED-4::CED-4 interaction, CED-4::CED-9 and CED-4::CED-3 interaction it was considered more important that the residue that only appeared in CED4::CED-4 interaction).

PDBsum use PDB codes as input. On the output screen 'Prot-prot' link was selected. This link provided the information regarding the interaction of CED-4 residues with other important proteins of the PCD process. The more times a CED-4 residue interacted with other important PCD proteins, then the more important it was considered (for example Arg50 appeared in CED-4::CED-4 interaction, CED-4::CED-9 interaction and CED-4::CED-3 interaction was assigned an interaction score of '3' as compared to an interaction score of '2 'assigned to His19 that only appeared in CED-4::CED-4 interaction and CED-4::CED-3 interaction). Similarly, interaction scores were given to each of the CED-4 residue.

3. Parameter 3: CED-4 protein structure

The third considered parameter for designing the CED-4 peptide segments was the structure of the CED-4 protein. Denatured CED-4 protein will not function. Since the CED-4 peptide segments must remain in the native form, the peptides were designed to include the complete secondary structural elements. The secondary structure of CED-4 was obtained from "The Secondary Structure Server" accessible at http://2struc.cryst.bbk.ac.uk/. The Secondary Structure Server compares eight different secondary structure assignment algorithms and gives the consensus protein sequence (Klose et al., 2010). The Secondary Structure Server was developed in 2010 in the Wallace Lab, Department of Crystallography, Institute of Structural and Molecular Biology, Birkbeck College, University of London and the Janes Lab, School of Biological and Chemical Sciences, Queen Mary, University of London, UK.

On the opening screen of the secondary structure server '2Struc' link was selected. On the next screen PDB ID for CED-4 (3lqq) was provided and 'Analyse the protein' link was selected. On the following screen under 'Available method' section 'Select All' was clicked and then 'Multiple Structure Alignment' was selected. All the residues of CED-4 that appeared in the consensus sequence of the secondary structure server were assigned a value of 1.

4. Parameter 4: CED-4 peptide segment surface accessibility

The fourth considered parameter was the surface accessibility of the CED-4 peptide segment. CED-4 protein, or effective CED-4 peptide, must have a surface interaction with certain nematode proteins in order to act as an effective nematicide. A software called Superficial (software that generates peptide segments based on the linear and non-linear surface interactions of the protein of interest) (Goede et al., 2005) was used in order to determine the surface of accessibility of CED-4 residues. The Superficial software used for this study was version 1.2, designed in 2005 at Berlin Center for Genome Based Bioinformatics, 3D Data Mining Group, Institute of Biochemistry, Charité, Monbijoustr.2, 10117 Berlin, Germany.

As shown in Table 1, based on the user defined parameters, Superficial software designed peptides of different lengths. The Table 1 headers are the seven user defined parameters used to design the peptides. Seven user defined parameters were used to design seven different sets of peptides. Each time a residue appeared in the Superficial software generated peptides, it was assigned a value of '1'. If a residue appeared in Superficial software generated peptides every time, it was assigned a maximum value of '7.'

TABLE 1

Seven Different Set of User Defined Parameters used in sfs software

| Serial number. | % of atom | Window size | % aa on surface | Min peptide length | Max peptide length | Min Strand length | Max peptide diameter |
|---|---|---|---|---|---|---|---|
| 1 | 70 | 7 | 70 | 7 | 10 | 5 | 20 |
| 2 | 70 | 8 | 70 | 7 | 10 | 5 | 20 |
| 3 | 70 | 10 | 70 | 7 | 10 | 5 | 20 |
| 4 | 70 | 10 | 70 | 11 | 20 | 5 | 20 |

TABLE 1-continued

Seven Different Set of User Defined Parameters used in sfs software

| Serial number. | % of atom | Window size | % aa on surface | Min peptide length | Max peptide length | Min Strand length | Max peptide diameter |
|---|---|---|---|---|---|---|---|
| 5 | 70 | 15 | 70 | 11 | 30 | 5 | 20 |
| 6 | 70 | 10 | 70 | 12 | 30 | 5 | 20 |
| 7 | 70 | 20 | 70 | 15 | 30 | 5 | 20 |

Based on the interaction properties, conservation score, protein structure, and surface accessibility data, twelve CED-4 peptides were designed and selected from the full length of CED-4 protein. Table 2 and FIG. 7 show the twelve designed and selected peptides. FIG. 7 is not exactly to scale, but generally depicts the locations of the CED-4 peptides in relation to the entire CED-4 protein.

TABLE 2

CED-4 Peptides of Protein Sequence Depicted in SEQ. ID No. 1 with Nematicide Potential

| No. | Peptide | CED-4 residue position | Length |
|---|---|---|---|
| 1 | $NH_3$—QSHLADFLEDYIDFAINE-COOH | 80-97 of SEQ. ID No. 1 | 18 |
| 2 | $NH_3$—DLLRPVVIAPQFSRQ-COOH | 99-113 of SEQ. ID No. 1 | 15 |
| 3 | $NH_3$—RQMLDRKLLLGNVPKQMTC-COOH | 112-130 of SEQ. ID No. 1 | 19 |
| 4 | $NH_3$—TCYIREYHVDRVI-COOH | 129-141 of SEQ. ID No. 1 | 14 |
| 5 | $NH_3$—ILLMLKSEDDLLNF-COOH | 207-220 of SEQ. ID No. 1 | 14 |
| 6 | $NH_3$—TSVVLKRMICNALI-COOH | 227-240 of SEQ. ID No. 1 | 14 |
| 7 | $NH_3$—DVEISNAASQTCEFIEVTSLE-COOH | 274-294 of SEQ. ID No. 1 | 21 |
| 8 | $NH_3$—MMFFKSCEPKTFEKMAQLNNKLESR-COOH | 334-358 of SEQ. ID No. 1 | 25 |
| 9 | $NH_3$—LVGVECITPYSYKSLAMALQR-COOH | 360-380 of SEQ. ID No. 1 | 21 |
| 10 | $NH_3$—ALLSGKRMPVLTFKI-COOH | 442-456 of SEQ. ID No. 1 | 15 |
| 11 | $NH_3$—VDAQTIANGISILEQRL-COOH | 468-484 of SEQ. ID No. 1 | 17 |
| 12 | $NH_3$—FPKFMQLHQKFY-COOH | 529-540 of SEQ. ID No. 1 | 12 |

FIG. 8 shows the process by which the twelve peptides, shown in Table 2 and FIG. 7, and having nematicide potential, were designed. As shown in FIG. 8, normalized scores were calculated for each of the four parameters such that normalized scores for each parameter fell between the value of 0 and the value of 1 for each CED-4 amino acid residue. The amino acid residue number is indicated along the bottom of the graph. In order to calculate the normalized conservation scores the conservation scores for each amino acid residue were multiplied by '−1'. The most negative score thus obtained was added to the score of each amino acid residue.

The score thus obtained for each amino acid residue was divided by the largest score in the entire data set. Normalized score for interaction properties was calculated by dividing the interaction score (for each amino acid) by 5 (as there were a total of 5 interactions under consideration so the maximum interaction score that could be assigned to any amino acid residue was 5).

For protein structure, each amino acid was either given a score of '0' or '1' depending upon if the amino acid appeared in the consensus sequence. The normalized sfs score was calculated by dividing sfs score for each amino acid by '7' as the maximum Superficial software generated score that was assigned to an amino acid was 7 (if it appeared every time in the Superficial software generated peptides).

Normalized scores from each of the four parameters were then added to calculate the cumulative total score. This cumulative total score was again normalized to calculate the normalized cumulative total so that the value of normalized cumulative total for each CED-4 amino acid residue fell between the value of 0 and the value of 1. In order to calculate the normalized cumulative total, the cumulative total (for each amino acid) was divided by the highest cumulative total score obtained in the cumulative total data set. Using this normalized cumulative total for each amino acid residue, box averages of 5 and then 7 and 11 residues were calculated.

Figure 8:
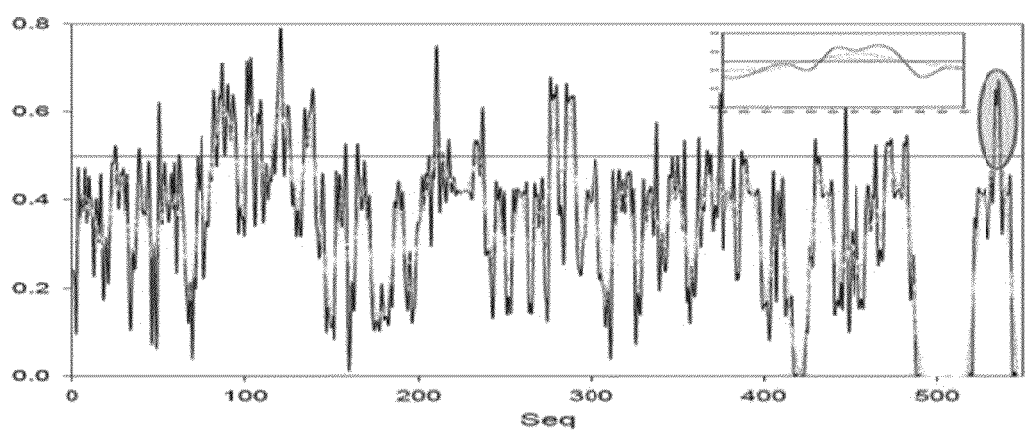

Box averages inform the overall effect of an amino acid region rather than the effect of a few amino acid residues in any particular region. A particular region of CED-4 could be important even if one or two amino acid residues in that region do not play the role towards its functionality. FIG. 8 shows the important regions or segments of CED-4 after box averages were calculated from the normalized cumulative total scores of each amino acid residue of CED-4 with cut off box score value of 0.5. The CED-4 segments above the cut-off value of 0.5 were selected as each of the twelve peptides shown in Table 2 and FIG. 4.

Figure 7:
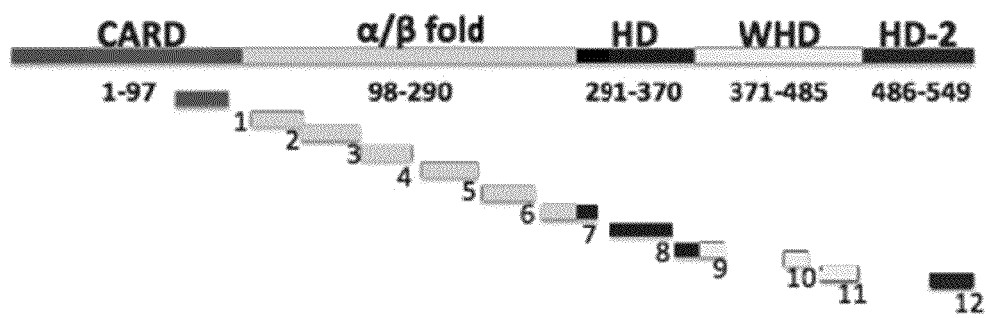
Figure 9:
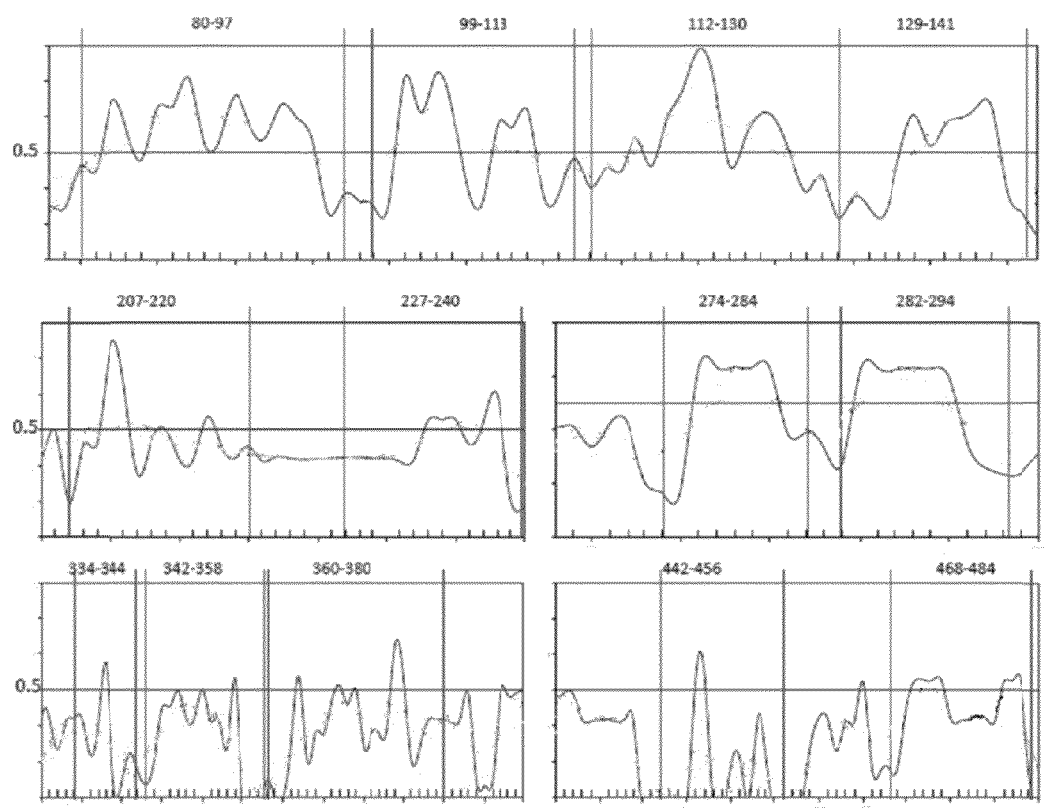

FIG. 9 is a detailed view of FIG. 8, specifically focusing on the amino acid regions of CED-4 that are above the cut off box score value of 0.5 that were selected to design the twelve peptides shown in Table 2 and FIG. 7. The amino acid residue number range is indicated at the top of the graphs. The peptide regions of CED-4 that are above the cut-off value of 0.5 are suitable for designing peptides because those regions each possess a high normalized cumulative total score, that was calculated using the four different parameters used to design these peptides.

F. SOME DESIGNED AND SELECTED CED-4 PEPTIDES ARE EFFECTIVE NEMATICIDES

After the twelve CED-4 peptides were designed and selected, as shown in Table 2 and FIG. 7, each of the twelve CED-4 peptides was tested to determine each peptide's efficacy at killing nematodes. CED-4 peptide eptide nos. 2, 3, and 12 were shown to be effective nematicides at a peptide concentration of about 0.8 mg/ml. At a concentration of about 0.8 mg/ml, each of peptide nos. 2, 3, and 12 killed 100% of the nematodes exposed to the peptide.

When the concentration was reduced to about 0.4 mg/ml, CED-4 peptide nos. 3, 10 and 12 were shown to be effective nematicides. At a concentration of about 0.4 mg/ml, CED-4 peptide no. 3 killed 60% of the nematodes exposed to the peptide. At a concentration of about 0.4 mg/ml, CED-4 peptide no. 10 killed 70% of the nematodes exposed to the peptide. At a concentration of about 0.4 mg/ml, CED-4 peptide no. 12 killed 66.7% of the nematodes exposed to the peptide.

The SEQ. ID 1 listed in this paragraph is identical to the sequence submitted in the text file named "CalderonSeqList0814_ST25" and which is herein incorporated by reference. The text file, identified in the preceding sentence and incorporated by reference, was created on Aug. 5, 2014 and is 5 kB in size. The CED-4 peptide no. 2 consists of amino acids 99 to 113 in the following SEQ. ID 1. The CED-4 peptide no. 3 consists of amino acids 112 to 130 in the following SEQ. ID 1. The CED-4 peptide no. 10 consists of amino acids 442 to 456 in the following SEQ. ID 1. The CED-4 peptide no. 12 consists of amino acids 529-to 540 in the following SEQ. ID 1.

```
SEQ. ID 1: CED-4 [Caenorhabditis elegans]
GenBank:CAA48781.1
http://www.ncbi.nlm.nih.gov/protein/CAA48781.1

1 MLCEIECRAL STAHTRLIHD FEPRDALTYL EGKNIFTEDH SELISKMSTR LERIANFLRI

61 YRRQASELGP LIDFFNYNNQ SHLADFLEDY IDFAINEPDL LRPVVIAPQF SRQMLDRKLL

121 LGNVPKQMTC YIREYHVDRV IKKLDEMCDL DSFFLFLHGR AGSGKSVIAS QALSKSDQLI

181 GINYDSIVWL KDSGTARKST FDLFTDILLM LKSEDDLLNF PSVEHVTSVV LKRMICNALI

241 DRPNTLFVFD DVVQEETIRW AQELRLRCLV TTRDVEISNA ASQTCEFIEV TSLEIDECYD

301 FLEAYGMPMP VGEKEEDVLN KTIELSSGNP ATLMMFFKSC EPKTFEKMAQ LNNKLESRGL

361 VGVECITPYS YKSLAMALQR CVEVLSDEDR SALAFAVVMP PGVDIPVKLW SCVIPVDICS

421 NEEEQLDDEV ADRLKRLSKR GALLSGKRMP VLTFKIDHII HMFLKHVVDA QTIANGISIL

481 EQRLLEIGNN NVSVPERHIP SHFQKFRRSS ASEMYPKTTE ETVIRPEDFP KFMQLEQKFY

541 DSLKNFACC
```

EXAMPLE 1

Nematicide Efficacy at 0.8 mg/ml Peptide Concentration

Assays were performed using 96-well plates. *C. elegans* nematodes at the L1 stage (refer to FIG. 1) were incubated in each of the 96 wells for three days at about 37° C. at about 0.8 mg/ml peptide concentration for each tested CED-4 peptide. Each of the selected CED-4 peptides were diluted in distilled water to 0.8 mg/ml peptide concentration. Nematodes—numbering between two nematodes and four nematodes—averaging about three nematodes were incubated in 100 μl of CED-4 peptide solution at about 0.8 mg/ml concentration in each well. After a three-day incubation period, the exposed *C. elegans* nematodes were checked for viability under a dissecting microscope. The nematodes that moved after being touched with a probe were considered alive, whereas the nematodes that showed no mobility after being touched with a probe were considered dead. The control solutions used were 0.8 mg/ml bovine serum albumin (BSA) (Sigma-Aldrich) and distilled water.

Table 3 shows the number of trial experiments, the number of successful experiments, the total number of dead *C. elegans* from an of the successful experiments, the total number of living *C. elegans* from an of the successful experiments, the percentage of living *C. elegans* from an of the successful experiments, and the percentage of dead *C. elegans* from an of the successful experiments. The percentage of dead *C. elegans* from all of the successful experiments is also referred to as the "mortality rate."

Each separate well containing nematodes was considered an independent trial experiment. A well in which all of the incubated nematodes were either clearly alive or clearly dead at the end of the incubation period was recorded as one successful experiment. A well in which some or all of the incubated nematodes could not clearly be determined as alive or dead at the end of the incubation period was recorded as one unsuccessful experiment. At a concentration of about 0.8 mg/ml, nine trial experiments were carried out for each of the twelve designed CED-4 peptides.

As shown in Table 3, three successful experiments were recorded for designed CED-4 peptide no. 2. *C. elegans* nematode incubation in 0.8 mg/ml concentration of CED-4 peptide no. 2 solution resulted in a total of nine nematodes counted as dead from the three successful experiments and a total of zero nematodes counted as alive from the three successful experiments. CED-4 peptide no. 2 at a concentration of 0.8 mg/ml is associated with a 100% *C. elegans* nematode mortality rate.

As shown in Table 3, seven successful experiments were recorded for designed CED-4 peptide no. 3. *C. elegans* nematode incubation in 0.8 mg/ml concentration of CED-4 peptide no. 3 solution resulted in a total of 20 nematodes counted as dead from the seven successful experiments and a total of zero nematodes counted as alive from the seven successful experiments. CED-4 peptide no. 3 at a concentration of 0.8 mg/ml is associated with a 100% *C. elegans* nematode mortality rate.

As shown in Table 3, one successful experiment was recorded for designed CED-4 peptide no. 4. *C. elegans* nematode incubation in 0.8 mg/ml concentration of CED-4 peptide no. 4 solution resulted in a total of two nematodes counted as dead from the one successful experiment and a total of two nematodes counted as alive from the one successful experiment. CED-4 peptide no. 4 at a concentration of 0.8 mg/ml is associated with a 50% *C. elegans* nematode mortality rate.

As shown in Table 3, one successful experiment was recorded for designed CED-4 peptide no. 10. *C. elegans* nematode incubation in 0.8 mg/ml concentration of CED-4 peptide no. 10 solution resulted in a total of one nematode counted as dead from the one successful experiment and a total of two nematodes counted as alive from the one successful experiment. CED-4 peptide no. 10 at a concentration of 0.8 mg/ml is associated with a 33.3% *C. elegans* nematode mortality rate.

As shown in Table 3, three successful experiments were recorded for designed CED-4 peptide no. 11. *C. elegans* nematode incubation in 0.8 mg/ml concentration of CED-4 peptide no. 11 solution resulted in a total of three nematodes counted as dead from the three successful experiments and a total of seven nematodes counted as alive from the three successful experiments. CED-4 peptide no. 11 at a concentration of 0.8 mg/ml is associated with a 30% *C. elegans* nematode mortality rate.

As shown in Table 3, three successful experiments were recorded for designed CED-4 peptide no. 12. *C. elegans* nematode incubation in 0.8 mg/ml concentration of CED-4 peptide no. 12 solution resulted in a total of seven nematodes counted as dead from the three successful experiments and a total of 0 nematodes counted as alive from the three successful experiments. CED-4 peptide no. 12 at a concentration of 0.8 mg/ml is associated with a 100% *C. elegans* nematode mortality rate.

CED-4 peptide nos. 1, 5, 6, 7, 8, and 9 each were not associated with a high number of dead nematodes in the successful experiments at a peptide concentration of 0.8 mg/ml.

TABLE 3

Designed Peptide Number with Number of Successful Experiments, Percentage Alive, and Percentage Dead of *C. elegans* at 0.8 mg/ml Concentration

| | Experiments | | # of nematodes | | | |
|---|---|---|---|---|---|---|
| | Successful | Total Trial | Dead in all combined | Alive in all combined | Percentage | |
| Peptide No. | Successful Experiments | Total Trial Experiments | successful experiments | successful experiments | % Dead | % Alive |
| 1 | 0 | 9 | NA | NA | NA | NA |
| 2 | 3 | 9 | 9 | 0 | 100 | 0 |
| 3 | 7 | 9 | 20 | 0 | 100 | 0 |
| 4 | 1 | 9 | 2 | 2 | 50 | 50 |
| 5 | 0 | 9 | NA | NA | NA | NA |
| 6 | 3 | 9 | 0 | 9 | 0 | 100 |
| 7 | 6 | 9 | 0 | 18 | 0 | 100 |
| 8 | 1 | 9 | 0 | 2 | 0 | 100 |
| 9 | 3 | 9 | 0 | 8 | 0 | 100 |
| 10 | 1 | 9 | 1 | 2 | 33.3 | 66.7 |
| 11 | 3 | 9 | 3 | 7 | 30 | 70 |
| 12 | 3 | 9 | 7 | 0 | 100 | 0 |
| BSA | 9 | 9 | 0 | 26 | 0 | 100 |
| Water | 9 | 9 | 0 | 29 | 0 | 100 |

EXAMPLE 2

Nematicide Efficacy at 0.4 mg/ml Peptide Concentration

In a second set of experiments, the designed CED-4 peptide concentration dispensed into the incubating wells was decreased from about 0.8 mg/ml to about 0.4 mg/ml to see if nematode mortality can be achieved with this lower concentration.

Assays were performed using 96-well plates. *C. elegans* nematodes at the L1 stage (refer to FIG. 1) were incubated in each of the 96 wells for three days at about 37° C. at about 0.4 mg/ml peptide concentration for each tested CED-4 peptide. Each of the selected CED-4 peptides were diluted in distilled water to 0.4 mg/ml peptide concentration. Nematodes—numbering between two nematodes and four nematodes—averaging about three nematodes were incubated in 100 μl of CED-4 peptide solution at about 0.4 mg/ml concentration in each well. After a three-day incubation period, the exposed *C. elegans* nematodes were checked for viability under a dissecting microscope. The nematodes that moved after being touched with a probe were considered alive, whereas the nematodes that showed no mobility after being touched with a probe were considered dead. The control solutions used were 0.4 mg/ml bovine serum albumin (BSA) (Sigma-Aldrich) and distilled water.

Table 4 shows the number of trial experiments, the number of successful experiments, the total number of dead *C. elegans* from all of the successful experiments, the total number of living *C. elegans* from all of the successful experiments, the percentage of living *C. elegans* from all of the successful experiments, and the percentage of dead *C. elegans* from all of the successful experiments. The percentage of dead *C. elegans* from all of the successful experiments is also referred to as the "mortality rate."

Each separate well containing nematodes was considered an independent trial experiment. A well in which all of the incubated nematodes were either clearly alive or clearly dead at the end of the incubation period was recorded as one successful experiment. A well in which some or all of the incubated nematodes could not clearly be determined as alive or dead at the end of the incubation period was recorded as one unsuccessful experiment. At a concentration of about 0.4 mg/ml, eight trial experiments were carried out for each of the twelve designed CED-4 peptides.

As shown in Table 4, three successful experiments were recorded for designed CED-4 peptide no. 2. *C. elegans* nematode incubation in 0.4 mg/ml concentration of CED-4 peptide no. 2 solution resulted in a total of one nematode counted as dead from the three successful experiments and a total of twelve nematodes counted as alive from the three successful experiments. CED-4 peptide no. 2 at a concentration of 0.4 mg/ml is associated with a 7.7% *C. elegans* nematode mortality rate.

As shown in Table 4, four successful experiments were recorded for designed CED-4 peptide no. 3. *C. elegans* nematode incubation in 0.4 mg/ml concentration of CED-4 peptide no. 3 solution resulted in a total of nine nematodes counted as dead from the four successful experiments and a total of six nematodes counted as alive from the four successful experiments. CED-4 peptide no. 3 at a concentration of 0.4 mg/ml is associated with a 60% *C. elegans* nematode mortality rate.

As shown in Table 4, five successful experiments were recorded for designed CED-4 peptide no. 4. *C. elegans* nematode incubation in 0.4 mg/ml concentration of CED-4 peptide no. 4 solution resulted in a total of five nematodes counted as dead from the five successful experiments and a total of nine nematodes counted as alive from the five successful experiments. CED-4 peptide no. 4 at a concentration of 0.4 mg/ml is associated with a 35.71% *C. elegans* nematode mortality rate.

As shown in Table 4, two successful experiments were recorded for designed CED-4 peptide no. 8. *C. elegans* nematode incubation in 0.4 mg/ml concentration of CED-4 peptide no. 8 solution resulted in a total of one nematode counted as dead from the two successful experiments and a total of 10 nematodes counted as alive from the two successful experiments. CED-4 peptide no. 8 at a concentration of 0.4 mg/ml is associated with a 9.09% *C. elegans* nematode mortality rate.

As shown in Table 4, three successful experiments were recorded for designed CED-4 peptide no. 10. *C. elegans* nematode incubation in 0.4 mg/ml concentration of CED-4 peptide no. 10 solution resulted in a total of seven nematodes counted as dead from the three successful experiments and a total of three nematodes counted as alive from the three successful experiments. CED-4 peptide no. 10 at a concentration of 0.4 mg/ml is associated with a 70% *C. elegans* nematode mortality rate.

As shown in Table 4, three successful experiments were recorded for designed CED-4 peptide no. 12. *C. elegans* nematode incubation in 0.4 mg/ml concentration of CED-4 peptide no. 12 solution resulted in a total of six nematodes counted as dead from the three successful experiments and a total of three nematodes counted as alive from the three successful experiments. CED-4 peptide no. 12 at a concentration of 0.4 mg/ml is associated with a 66.7% *C. elegans* nematode mortality rate.

CED-4 peptide nos. 1, 5, 6, 7, 9 and 11 each were not associated with a high number of dead nematodes in the successful experiments at a peptide concentration of 0.4 mg/ml.

TABLE 4

Designed Peptide Number with Number of Successful Experiments, Percentage Alive, and Percentage Dead *C. elegans* at 0.4 mg/ml Concentration

| | Experiments | | # of nematodes | | | |
| --- | --- | --- | --- | --- | --- | --- |
| | Successful | Total Trial | Dead in all combined | Alive in all combined | Percentage | |
| Peptide No. | Experiments | Experiments | successful experiments | successful experiments | % Dead | % Alive |
| 1 | 4 | 8 | 0 | 14 | 0 | 100 |
| 2 | 3 | 8 | 1 | 12 | 7.7 | 92.3 |
| 3 | 4 | 8 | 9 | 6 | 60 | 40 |
| 4 | 5 | 8 | 5 | 9 | 35.71 | 64.28 |
| 5 | 0 | 8 | NA | NA | NA | NA |
| 6 | 3 | 8 | 0 | 9 | 0 | 100 |
| 7 | 6 | 8 | 0 | 19 | 0 | 100 |
| 8 | 2 | 8 | 1 | 10 | 9.09 | 90.90 |
| 9 | 6 | 8 | 0 | 18 | 0 | 100 |
| 10 | 3 | 8 | 7 | 3 | 70 | 30 |
| 11 | 7 | 8 | 0 | 22 | 0 | 100 |
| 12 | 3 | 8 | 6 | 3 | 66.7 | 33.3 |
| BSA | 7 | 8 | 0 | 21 | 0 | 100 |
| Water | 7 | 8 | 0 | 21 | 0 | 100 |

A number of embodiments of the invention have been described. Nevertheless, it will be understood that various modifications may be made without departing from the spirit and scope of the invention. Accordingly, other embodiments are within the scope of the present invention.

We claim:

1. A nematicide composition comprising an effective amount of a designed CED-4 peptide consisting of no more than 50 consecutive amino acids of SEQ. ID No. 1, wherein two amino acid residues are mutated.

2. A nematicide composition according to claim 1, wherein said designed CED-4 peptide consists of no more than 30 consecutive amino acids of SEQ. ID No. 1, wherein two amino acid residues are mutated.

3. A nematicide composition according to claim 1, wherein said designed CED-4 peptide consists of no more than 20 consecutive amino acids of SEQ. ID No. 1, wherein two amino acid residues are mutated.

4. A nematicide composition according to claim 1, wherein said designed CED-4 peptide consists of amino acid sequence 112-130 of SEQ ID No. 1, wherein two amino acid residues are mutated.

5. A nematicide composition according to claim 1, wherein said CED-4 peptide consists of amino acid sequence 99-113 of SEQ ID No. 1.

6. A nematicide composition according to claim 1, wherein said CED-4 peptide consists of amino acid sequence 529-540 of SEQ ID No. 1.

7. A nematicide composition according to claim 1, wherein said nematicide is administered to plant parasitic nematodes.

8. A nematicide composition according to claim 1, wherein said nematicide is administered to nematodes from genus *Meloidogyne*.

9. A nematicide composition according to claim 1, wherein said effective amount consists of a designed CED-4 peptide concentration of about 0.8 mg/ml.

* * * * *